(12) United States Patent
Lee et al.

(10) Patent No.: US 11,202,815 B2
(45) Date of Patent: Dec. 21, 2021

(54) COMPOSITION FOR PREVENTING, TREATING OR IMPROVING PROSTATE DISEASE CONTAINING ACANTHOPANAX SESSILIFLORUS, PHRAGMITES RHIZOME, AND PINUS DENSIFLORA EXTRACTS AS ACTIVE INGREDIENT

(71) Applicant: GENOME & MEDICINE CO., LTD., Seoul (KR)

(72) Inventors: Min Won Lee, Seoul (KR); Kyu Hyeong Yoon, Seoul (KR); Yoon Ok Lee, Seoul (KR); Sung Hye Youn, Busan (KR); Jae Seung Yoon, Seoul (KR)

(73) Assignee: GENOME & MEDICINE CO., LTD., Seoul (KR)

( * ) Notice: Subject to any disclaimer, the term of this patent is extended or adjusted under 35 U.S.C. 154(b) by 470 days.

(21) Appl. No.: 16/331,302

(22) PCT Filed: Nov. 19, 2018

(86) PCT No.: PCT/KR2018/014166
§ 371 (c)(1),
(2) Date: Mar. 7, 2019

(87) PCT Pub. No.: WO2019/124757
PCT Pub. Date: Jun. 27, 2019

(65) Prior Publication Data
US 2021/0322501 A1    Oct. 21, 2021

(30) Foreign Application Priority Data

Dec. 19, 2017   (KR) .................. 10-2017-0175089

(51) Int. Cl.
A61K 36/00    (2006.01)
A61K 36/254   (2006.01)
(Continued)

(52) U.S. Cl.
CPC .......... A61K 36/254 (2013.01); A23L 33/105 (2016.08); A23L 33/40 (2016.08);
(Continued)

(58) Field of Classification Search
CPC ..................................................... A61K 36/00
See application file for complete search history.

(56) References Cited

FOREIGN PATENT DOCUMENTS

| KR | 10-2006-0067255 A | 6/2006 |
| KR | 10-0882780 B1 | 2/2009 |

(Continued)

OTHER PUBLICATIONS

English abstract of Gyeong et al., KR 1301546 B1, 2013.*
English abstractor Dong et al., KR 1795261 B1, Nov. 7, 2017.*

Primary Examiner — Rosanne Kosson
(74) Attorney, Agent, or Firm — Revolution IP, PLLC

(57) ABSTRACT

The present invention relates to a composition for preventing, treating or improving a prostate disease containing *Acanthopanax sessiliflorus*, *Phragmites* rhizome, and *Pinus densiflora* extracts as an active ingredient. According to the present invention, the complex extract of *Acanthopanax sessiliflorus*, *Phragmites* rhizome, and *Pinus densiflora* has an effect of inhibiting the activity of 5α-reductase associated with benign prostatic hyperplasia and has an advantage of having a few or no side effects of reducing a male sexual function by using a synthetic compound in the related art using ingredients derived from natural plants. Further, it is confirmed that in a complex extract obtained by mixing *Acanthopanax sessiliflorus*, *Phragmites* rhizome, and *Pinus densiflora* extracts at a more proper ratio, the 5α-reductase inhibitory activity is significantly excellent.

7 Claims, 8 Drawing Sheets

| IC$_{50}$ | | | | | | | | | | | | | |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 108.3 | -240.4 | 333.9 | 199.6 | 211.8 | 322.7 | 316.7 | 623.7 | -380.6 | 79.8 | 116.1 | 85.2 | 40.9 | 11.9 |

1. acanthoside D
2. Syringin
3. Methyl gallate
4. P-coumaric acid
5. Lyoniresinol
6. Lyoniresinol-glucopyranoside
7. Catechine
8. Taxifolin
9. Procyanidin B1
10. Pinus densiflora extract
11. Phragmites rhizome extract
12. Acanthopanax sessiliflorus extract
13. Complex extract
14. Finasteride

(51) Int. Cl.
*A61K 36/899* (2006.01)
*A61K 36/15* (2006.01)
*A61P 13/08* (2006.01)
*A23L 33/00* (2016.01)
*A23L 33/105* (2016.01)
*A61K 9/00* (2006.01)

(52) U.S. Cl.
CPC ............ *A61K 9/0056* (2013.01); *A61K 36/15* (2013.01); *A61K 36/899* (2013.01); *A61P 13/08* (2018.01); *A23V 2002/00* (2013.01)

(56) References Cited

FOREIGN PATENT DOCUMENTS

| | | |
|---|---|---|
| KR | 10-2013-0081131 A | 7/2013 |
| KR | 10-2014-0015199 A | 2/2014 |
| KR | 10-1381831 B1 | 4/2014 |

* cited by examiner

FIG. 2

| | | | | | | | IC50 | | | | | | |
|---|---|---|---|---|---|---|---|---|---|---|---|---|---|
| 1 | 2 | 3 | 4 | 5 | 6 | 7 | 8 | 9 | 10 | 11 | 12 | 13 | 14 |
| 108.3 | -240.4 | 333.9 | 199.6 | 211.8 | 322.7 | 316.7 | 623.7 | -380.6 | 79.8 | 116.1 | 85.2 | 40.9 | 11.9 |

1. acanthoside D
2. Syringin
3. Methyl gallate
4. P-coumaric acid
5. Lyoniresinol
6. Lyoniresinol-glucopyranoside
7. Catechine
8. Taxifolin
9. Procyanidin B1
10. Pinus densiflora extract
11. Phragmites rhizome extract
12. Acanthopanax sessiliflorus extract
13. Complex extract
14. Finasteride

FIG. 6

| Compound 1 | Conc. (μg/mℓ) | Accuracy(%) | | Precision (C.V., %) | |
|---|---|---|---|---|---|
| | | Intra-day | Intra-day | Intra-day | Intra-day |
| Acanthoside D | 62.5 | 96.77 | 97.36 | 0.86 | 0.85 |
| | 125 | 100.30 | 99.59 | 0.85 | 0.77 |
| | 250 | 101.19 | 101.46 | 1.13 | 0.75 |
| | 500 | 99.74 | 99.70 | 0.60 | 0.46 |
| P-Coumaric Acid | 31.25 | 96.39 | 97.81 | 0.21 | 0.20 |
| | 62.5 | 100.96 | 100.49 | 0.46 | 0.57 |
| | 125 | 100.86 | 100.59 | 0.62 | 0.39 |
| | 250 | 99.78 | 99.86 | 0.12 | 0.40 |

COMPOSITION FOR PREVENTING, TREATING OR IMPROVING PROSTATE DISEASE CONTAINING ACANTHOPANAX SESSILIFLORUS, PHRAGMITES RHIZOME, AND PINUS DENSIFLORA EXTRACTS AS ACTIVE INGREDIENT

CROSS REFERENCE TO RELATED APPLICATION

This present application is a national stage filing under 35 U.S.C § 371 of PCT application number PCT/KR2018/014166 filed on Nov. 19, 2018 which is based upon and claims the benefit of priority to Korean Patent Application No. 10-2017-0175089 filed on Dec. 19, 2017 in the Korean Intellectual Property Office. The disclosures of the above-listed applications are hereby incorporated by reference herein in their entirety.

TECHNICAL FIELD

The present invention relates to a composition for preventing, treating or improving a prostate disease containing *Acanthopanax sessiliflorus, Phragmites* rhizome, and *Pinus densiflora* extracts as an active ingredient.

BACKGROUND ART

Testosterone 5α-reductase converts testosterone, one of the male hormones, to dihydrotestosterone (DHT), an active male hormone, and one of the diseases caused by the activated dihydrotestosterone is benign prostatic hyperplasia.

In the related art, the benign prostatic hyperplasia was defined as a state in which the prostate is enlarged to block the passage of the urine under the bladder, causing the urethral obstruction and thus the flow of urine is reduced, and histologically, defined as proliferating prostate stromal cells or epithelial cells of prostate.

However, recently, since the pathophysiology of the disease is too complicated to explain the definition or concept as described above, the benign prostatic hyperplasia has been defined as lower urinary tract symptoms which are collectively known as symptoms of bladder storage such as origiuria in which men who are over 50 years old urinate more than 8 times a day, nycturia, and urgency in which men can not stand urinating while feeling strong and sudden urinating (feeling urine), and symptoms of bladder excretion obstruction such as delayed urine (a phenomenon that urine comes out after a little bit when urinating), discontinuous urine (a phenomenon in which the flow of the urine is discontinued), and a phenomenon of giving strength when urinating.

The disease may be treated with drugs, and may be treated by administering an androgen inhibitor among the drugs.

A testosterone 5α-reductase inhibitor, one of the androgen inhibitors, is used as a therapeutic agent for benign prostatic hyperplasia (International Patent Application Publication No. 1994-7000080), and finasteride and dutasteride have been sold on the market.

These drugs act to reduce the size of the prostate by inhibiting the action of androgen in the androgen-sensitive prostate.

In recent studies, it has been reported as results that in long-term use, these drugs are beneficial in reducing the progression of benign prostatic hyperplasia by reducing acute urinary retention and frequency of surgery. However, these medications are recommended only at high prostate-specific antigen (PSA) levels and a large size of the prostate.

Causal treatment is possible due to the resection of the enlarged prostate tissue by the surgical treatment and medication, but most of the patients are the elderly and the operation is limited, and there are problems such as post-operative side effects and recurrence.

In addition, the 5-alpha-reductase inhibitor is largely dependent on imports to impose no little burden on the national economy, and has a long time taken until effects after administration are exhibited, and side effects such as dizziness, fatigue and excessive hypotension as well as side effects of reducing male sexuality such as loss of sexual desire and erectile dysfunction, and thus there is a growing expectation for the development of new natural product drugs.

Meanwhile, *Acanthopanax sessiliflorus* is called the bark of roots, stems and branches of *Acanthopanax sessiliflorum* seeman or *Acanthopanax* species, and the *Acanthopanax sessiliflorus* was called oga and then written as oga because a left is divided into five parts, and it is good to have five leaves on one branch.

The pharmacological actions of *Acanthopanax sessiliflorus* have been reported to be immune enhancement, anti-oxidant, anti-fatigue, anti-hypertension, anti-irritation, endocrine control, blood pressure control, anti-radioactivity and detoxification.

Further, *Phragmites* rhizome refers to a rhizome of *Phragmites communis* trinius and called reed that does not yet bloom into ears.

The *Phragmites* rhizome is used for symptoms of stuffy and uncomfortable chest, dry resin due to fever, dry thirst and burning of the mouth by lowering lung fever.

The *Phragmites* rhizome lowers the gastric fever to stop the nausea, sickness and vomiting. It has been reported that the *Phragmites* rhizome is used for chronic cough, sputum, pulmonary tuberculosis and lung abscess due to lung fever and detoxifies fish poison. It has been reported that as pharmacological actions, there are a diuretic effect, an antipyretic effect, a liver protective effect and a hematopoietic function enhancement effect.

In addition, the *Pinus densiflora* is an evergreen tree belonging to pinaceae, which is called pine, pine tree, and soon tree, and its seed has an oval shape with a length of 5 to 6 mm and a width of 3 mm and a black brown color and the pinnae are light brown with dark brown lines.

The leaves are used for indigestion or tongue agent, flowers are used for dysentery, and rosin used for medicinal use for raw materials of plaster, respectively. The pollen is used as songgwa powder to make dasik, the bark is edible by making a songgyi rice cake and used for building material and pulp wood, and turpentine is used as raw materials for paint, varnish and synthetic camphor. From old times, the *Pinus densiflora* has been planted many times as ornamental trees, pavilion trees, trees scared to the gods, and scared trees.

However, an activity inhibitory effect and a therapeutic effect on prostate diseases of 5α-reductase of *Acanthopanax sessiliflorus, Phragmites* rhizome, and *Pinus densiflora* extracts have not been found yet.

DISCLOSURE

Technical Problem

An object of the present invention is to provide a pharmaceutical composition for preventing or treating a prostate disease containing *Acanthopanax sessiliflorus*, *Phragmites* rhizome, and *Pinus densiflora* extracts as an active ingredient.

Another object of the present invention is to provide a health functional food composition for preventing or improving a prostate disease containing *Acanthopanax sessiliflorus*, *Phragmites* rhizome, and *Pinus densiflora* extracts as an active ingredient.

However, technical objects of the present invention are not limited to the aforementioned purpose and other objects which are not mentioned may be clearly understood to those skilled in the art from the following description.

Technical Solution

In order to solve the problems, the present invention provides a pharmaceutical composition for preventing or treating a prostate disease containing *Acanthopanax sessiliflorus*, *Phragmites* rhizome, and *Pinus densiflora* extracts as an active ingredient.

Further, the present invention provides a health functional food composition for preventing or improving a prostate disease containing *Acanthopanax sessiliflorus*, *Phragmites* rhizome, and *Pinus densiflora* extracts as an active ingredient.

In one embodiment of the present invention, the composition may inhibit 5α-reductase activity.

In another embodiment of the present invention, the prostate disease may be benign prostatic hyperplasia.

In yet another embodiment of the present invention, the *Acanthopanax sessiliflorus*, *Phragmites* rhizome, and *Pinus densiflora* extracts may be extracted with at least one solvent selected from the group consisting of water, alcohols having 1 to 4 carbon atoms, n-hexane, ethyl acetate, acetone, butyl acetate, 1,3-butylene glycol, methylene chloride, and mixed solvents thereof.

In still another embodiment of the present invention, the composition may include 2 to 5 parts by weight of the *Acanthopanax sessiliflorus* extract with respect to 1 part by weight of the *Pinus densiflora* extract.

In still yet another embodiment of the present invention, the composition may include 1 to 3 parts by weight of the *Phragmites* rhizome extract with respect to 1 part by weight of the *Pinus densiflora* extract.

In still yet another embodiment of the present invention, the composition may include 4 parts by weight of the *Acanthopanax sessiliflorus* extract and 2 parts by weight of the *Phragmites* rhizome extract with respect to 1 part by weight of the *Pinus densiflora* extract.

Further, the present invention provides a method for treating a prostate disease including administering a composition containing *Acanthopanax sessiliflorus*, *Phragmites* rhizome, and *Pinus densiflora* extracts to a subject.

Further, the present invention provides a use for treating a prostate disease of a composition containing *Acanthopanax sessiliflorus*, *Phragmites* rhizome, and *Pinus densiflora* extracts.

Advantageous Effects

According to the present invention, the complex extract of *Acanthopanax sessiliflorus*, *Phragmites* rhizome, and *Pinus densiflora* has an effect of inhibiting the activity of 5α-reductase associated with benign prostatic hyperplasia and has an advantage of having a few or no side effects of reducing a male sexual function by using a synthetic compound in the related art using ingredients derived from natural plants.

Further, it is confirmed that in a complex extract obtained by mixing *Acanthopanax sessiliflorus*, *Phragmites* rhizome, and *Pinus densiflora* extracts at a more proper ratio, the 5α-reductase inhibitory activity is significantly excellent. The complex extract contributes to the national economy by replacing synthetic compounds that have been dependent on import to prevent or treat benign prostatic hyperplasia. The complex extract will be used for various fields such as medicines, external use medicines, functional biomaterials, and functional food materials, as an agent of preventing or treating benign prostatic hyperplasia in which side effects of an existing 5α-reductase inhibitor are reduced.

DESCRIPTION OF DRAWINGS

FIG. 2 is a diagram for confirming inhibitory activity of 5α-reductase of the complex extract.

FIG. 6 is a diagram illustrating precision and accuracy of acanthoside D and p-coumaric acid which are efficacy index ingredients of the complex extract.

MODES OF THE INVENTION

Figure 1:
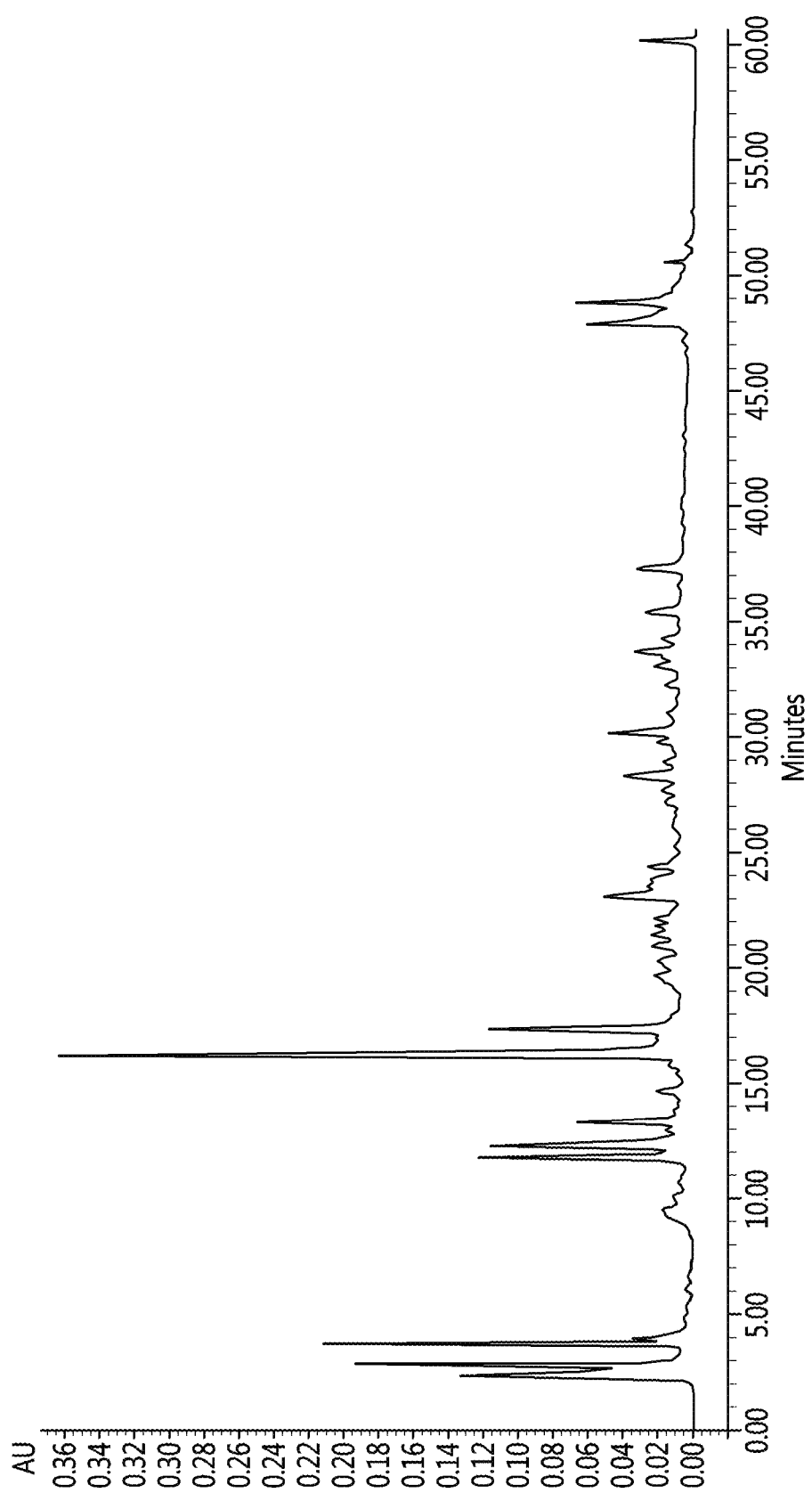
FIG. 1 is a diagram illustrating an HPLC result of a complex extract.

The present inventors conducted many studies to develop therapeutic agents for prostate diseases derived from natural substances, and as a result, confirmed that *Acanthopanax sessiliflorus*, *Phragmites* rhizome, and *Pinus densiflora* extracts had 5α-reductase inhibitory activity and particularly, confirmed that a complex extract in which *Acanthopanax sessiliflorus*, *Phragmites* rhizome, and *Pinus densiflora* extracts are mixed with a weight ratio of 4:2:1 had significantly excellent 5α-reductase inhibitory activity, and then completed the present invention.

The present inventors confirmed that a complex extract of *Acanthopanax sessiliflorus*, *Phragmites* rhizome, and *Pinus densiflora* had excellent 5 alpha-reductase inhibitory activity by comparing an *Acanthopanax sessiliflorus* extract, a *Phragmites* rhizome extract, or a *Pinus densiflora* extract and a complex extract in which the extracts were mixed in 5α-reductase inhibitory activity using a synthetic 5α-reductase inhibitor as a positive control (see Example 3), confirmed efficacy index compounds of acanthoside D and p-coumaric acid in each extract (see Example 4), and confirmed through a detailed experiment that 1.06% of acanthoside D and 0.07% of p-coumaric acid were contained in the complex extract of *Acanthopanax sessiliflorus*, *Phragmites* rhizome, and *Pinus densiflora* (see Example 5).

In this specification, the *Acanthopanax sessiliflorus* refers to the bark of roots, stems and branches of *Acanthopanax sessiliflorum* seeman or *Acanthopanax* species, the *Phragmites* rhizome refers to a rhizome of *Phragmites communis* trinius, and the *Pinus densiflora* is an evergreen tree belonging to pinaceae, which is called pine and pine tree.

There are no physiological studies related to the 5α-reductase inhibitory activity of *Acanthopanax sessiliflorus, Phragmites* rhizome, and *Pinus densiflora* extracts.

In this specification, the extract includes an extract itself and extracts of all formulations of extracts that can be formed using the extract, such as an extract obtained by extracting the *Acanthopanax sessiliflorus*, the *Phragmites* rhizome, or the *Pinus densiflora*, a diluted solution or concentrate of the extract, a dried product obtained by drying the extract, a controlled preparation or a purified product of the extract, or mixtures thereof. A complex extract is obtained by mixing the *Acanthopanax sessiliflorus, Phragmites* rhizome, and *Pinus densiflora* extracts with a proper weight ratio and may include 2 to 5 parts by weight of the *Acanthopanax sessiliflorus* extract and/or 1 to 3 parts by weight of the *Phragmites* rhizome extract with respect to 1 part by weight of the *Pinus densiflora* extract, but is not limited thereto.

In addition, according to an embodiment of the present invention, the mixed extract may be obtained by mixing *Acanthopanax sessiliflorus, Phragmites* rhizome, and *Pinus densiflora* with a weight ratio of 4:2:1, but is not limited thereto.

In the obtaining of the *Acanthopanax sessiliflorus, Phragmites* rhizome, and *Pinus densiflora* extracts of the present invention, an extraction method is not particularly limited and the extracts may be extracted according to methods commonly used in the art.

Non-limiting examples of the extraction method may include a hydrothermal extraction method, an ultrasonic extraction method, a filtration method, and a reflux extraction method, and these methods may be performed alone or in combination with two or more methods.

In the present invention, a type of extraction solvent used for obtaining the *Acanthopanax sessiliflorus, Phragmites* rhizome, and *Pinus densiflora* extracts is not particularly limited and may use any solvent known in the art.

Non-limiting examples of the extraction solvent may include water; C1 to C4 lower alcohols such as methanol, ethanol, propyl alcohol and butyl alcohol; polyhydric alcohols such as glycerin, butylene glycol and propylene glycol; and hydrocarbon solvents such as methyl acetate, ethyl acetate, acetone, benzene, hexane, diethyl ether and dichloromethane; or mixtures thereof.

Further, the *Acanthopanax sessiliflorus, Phragmites* rhizome, and *Pinus densiflora* extracts of the present invention may be subjected to extraction and/or fractionation and then subjected to a reduced pressure filtration process or further subjected to concentration and/lyophilization to be concentrated or remove the solvent, and each of the harvested plant extracts may be stored in a rapid freezing refrigerator until use.

In this specification, prostate diseases refer to various diseases that occur in the male prostate, and may be preferably prostate cancer, benign prostatic hyperplasia, prostatitis, prostatovesiculitis or utriculitis, and more preferably, benign prostatic hyperplasia.

Further, in this specification, the benign prostatic hyperplasia (BPH) is a disease in which the prostate is enlarged due to various reasons and includes lower urinary tract symptoms (LUTS) in which the mucous secreting gland, such as the collum of the urethra or bladder and the bladder trigone, or the urination conduct is enlarged.

Patients with benign prostatic hyperplasia have symptoms which can not tolerate urine, have thin and weak urine, hesitate for quite a while when urinating, or feel feeling of residual urine after urination.

Further, in this specification, the 5α-reductase is an enzyme of converting testosterone into dihydrotstosterone (DHT), a main male hormone involved in the growth of prostate tissue, in the prostate, and a use of a 5α-reductase inhibitor for the treatment of the benign prostatic hyperplasia has reached an obvious level to those skilled in the art.

However, the use of a synthetic 5α-reductase inhibitor has a long time taken until effects after administration are exhibited, and side effects such as dizziness, fatigue and excessive hypotension as well as side effects of reducing male sexuality such as loss of sexual desire and erectile dysfunction, and thus it is necessary to develop new natural product drugs.

Thus, the present inventors have confirmed 5α-reductase inhibitory activity on a complex extract of *Acanthopanax sessiliflorus, Phragmites* rhizome, and *Pinus densiflora* extracts, and provide the complex extract for preventing, treating, or improving benign prostatic hyperplasia.

In the present invention, "prevention" means all actions that inhibit or delay the occurrence, spread or recurrence of prostate diseases upon administration of the composition of the present invention, and "treatment" means all actions which improve or beneficially change the symptoms of the diseases upon administration of the composition of the present invention.

Therefore, the present invention may provide a method for treating prostate diseases including administering, to a subject, a pharmaceutical composition for preventing or treating a prostate disease containing a complex extract of *Acanthopanax sessiliflorus, Phragmites* rhizome, and *Pinus densiflora* as an active ingredient. The prostate disease may be a disease selected from the group consisting of prostate cancer, benign prostatic hyperplasia, prostatitis, prostatovesiculitis, and utriculitis, preferably benign prostatic hyperplasia, but is not limited thereto.

In the present invention, the subject may be a mammal such as a mouse, a domestic animal, a rat, a human, particularly, a companion dog, a racehorse, a human, and the like requiring the treatment of the disease, and preferably a human.

The pharmaceutical composition for preventing or treating a prostate disease containing the complex extract of *Acanthopanax sessiliflorus, Phragmites* rhizome, and *Pinus densiflora* according to the present invention may be formulated and used in forms of external preparations such as powders, granules, tablets, capsules, suspensions, emulsions, syrups, aerosols, etc. and sterile injection solutions according to each general method and preferably, may have a formulation of a cream, a gel, a patch, a spray, an ointment, a plaster, a lotion, a liniment, a pasta or a cataplasma.

A carrier, an excipient, and a diluent which may be included in the composition containing the complex extract may be a quince extract, a cherry extract, lactose, dextrose, sucrose, oligosaccharide, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil.

When the composition is formulated, the formulation may be prepared by using a diluent or an excipient, such as a filler, an extender, a binder, a wetting agent, a disintegrating agent, and a surfactant, which are generally used.

A solid formulation for oral administration includes a tablet, a pill, a powder, a granule, a capsule, and the like, and the solid formulation may be prepared by mixing at least one excipient, for example, starch, calcium carbonate, sucrose or lactose, gelatin, and the like with the extract.

Further, lubricants such as magnesium stearate talc may be used in addition to simple excipients.

A liquid formulation for oral administration corresponds to a suspension, an oral liquid, an emulsion, a syrup, and the like, and may include various excipients, for example, a wetting agent, a sweetening agent, an aromatic agent, a preserving agent, and the like in addition to water and liquid paraffin which are commonly used simple diluents.

A formulation for parenteral administration includes a sterile aqueous solution, a non-aqueous solution, a suspension, an emulsion, and a lyophilizing agent, and a suppository.

As the non-aqueous solution and the suspension, propylene glycol, polyethylene glycol, vegetable oils such as olive oil, injectable ester such as ethyl oleate, and the like may be used.

As a base compound of the suppository, witepsol, macrogol, tween 61, cacao butter, laurin, glycerogelatin, and the like may be used.

A preferable dose of the pharmaceutical composition of the present invention varies according to a state and a weight of a patient, the degree of the disease, a drug form, and administration route and period, but may be properly selected by those skilled in the art.

The administration may be performed once or several times a day.

The dose does not limit the scope of the present invention in any aspect.

Further, the present invention provides a health functional food composition for preventing or improving a prostate disease containing a complex extract of *Acanthopanax sessiliflorus*, *Phragmites* rhizome, and *Pinus densiflora* as an active ingredient.

Further, the complex extract of *Acanthopanax sessiliflorus*, *Phragmites* rhizome, and *Pinus densiflora* may be added to foods for the purpose of prostate health.

When the complex extract of *Acanthopanax sessiliflorus*, *Phragmites* rhizome, and *Pinus densiflora* of the present invention is used as a food additive, the complex extract may be added as it is or used together with other foods or food ingredients, and may be properly used according to a general method.

The mixed amount of the active ingredients may be suitably determined according to the purpose of use (prevention, health, or therapeutic treatment).

The kind of food is not particularly limited.

Examples of the foods which may be added with the materials include meat, sausages, bread, chocolate, candies, snacks, cookies, pizza, ramen, other noodles, gums, dairy products including ice cream, various soups, beverages, tea, drinks, alcohol drinks, vitamin complex, and the like, and include all health functional foods in the accepted meaning.

In the health beverage composition according to the present invention, like a general beverage, various flavoring agents or natural carbohydrates may be added as an additional ingredient.

The above-mentioned natural carbohydrates include monosaccharides such as glucose and fructose, disaccharides such as maltose and sucrose, polysaccharides such as dextrin and cyclodextrin, and sugar alcohols such as xylitol, sorbitol and erythritol.

As the sweetening agent, natural sweetening agents such as thaumatin and a *stevia* extract, synthetic sweetening agents such as saccharin and aspartame, and the like may be used.

A ratio of the natural carbohydrate may be generally about 0.01 to 0.20 g and preferably about 0.04 to 0.10 g per 100 mL of the composition of the present invention.

The composition of the present invention may contain various nutrients, vitamins, electrolytes, flavoring agents, coloring agents, pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, or the like in addition to the ingredients.

Besides, the composition of the present invention may include pulps for preparing natural fruit juices, fruit juice beverages, and vegetable beverages.

These ingredients may be used independently or in combination. Although the ratio of the additives is not very important, generally, the ratio is selected in a range of 0.01 to 0.20 part by weight per 100 parts by weight of the composition of the present invention.

The present invention may have various modifications and various embodiments and specific embodiments will be illustrated in the drawings and described in detail in the detailed description.

However, this does not limit the present invention within specific embodiments, and it should be understood that the present invention covers all the modifications, equivalents and replacements within the idea and technical scope of the present invention.

In describing the present invention, a detailed description of related known technologies will be omitted if it is determined that they make the gist of the present invention unclear.

Hereinafter, a preferred embodiment is presented in order to assist understanding of the present invention. However, the following embodiment is just provided to more easily understand the present invention and contents of the present invention are not limited by the embodiment.

EXAMPLE

Example 1. Preparation of Complex Extract of *Acanthopanax Sessiliflorus*, *Phragmites* Rhizome, and *Pinus Densiflora*

Dried *Acanthopanax sessiliflorus*, *Phragmites* rhizome, and *Pinus densiflora* were added in a solvent and heated, respectively, to obtain extracts thereof, and the extracts were concentrated to prepare a concentrated extract of each extract.

The concentrated extracts were lyophilized and powdered, and then used.

Hereinafter, a complex extract of mixing *Acanthopanax sessiliflorus*, *Phragmites* rhizome, and *Pinus densiflora* extracts was prepared with a mixed ratio of 4:2:1 for each extract.

Example 2. Confirmation of Phytochemicals of *Acanthopanax Sessiliflorus*, *Phragmites* Rhizome, and *Pinus Densiflora* Extracts Bonded phase chromatography uses a property of being separated by the affinity with each active compound between fixed and mobile phases.

The fixed phase is divided into a normal-phase and a reverse-phase depending on a functional group of the fixed phase, and in the normal-phase, the fixed phase uses a polar solvent (e.g., silica gel) and the mobile phase uses a non-polar organic solvent, and each active compound is separated by a speed difference by strong chemical bonding (ionic bonding, etc.) and separation between a molecule and the polar fixed phase.

In the reverse-phase, since a functional group (C18, C8, alkyl group, aromatic phenyl group, amine group, etc.) bonded on a silica gel surface is used as the fixed phase (e.g., ODS gel) and a polar organic solvent is used as a mobile phase, and each active compound is separated by a speed difference due to bonding by non-specific hydrophobic interaction between the molecule and the non-polar fixed phase and separation, the reverse-phase may be used for separation of almost all organic materials with hydrophobic groups in the molecule.

Therefore, according to each characteristic and situation, index ingredients of *Acanthopanax sessiliflorus*, *Phragmites* rhizome, and *Pinus densiflora* were separated by using Sephadex LH-20, MCI-gel CHP 20P, ODS-B gel and silica gel 60.

Specifically, various compounds, such as acanthoside D separated from *Acanthopanax sessiliflorus*, methyl gallate, p-hydro cinnamic acid, (+)-lyoniresinol, and (+)-lyoniresinol-3α-O-β-D-glucopyranoside separated from *Phragmites* rhizome, and (+)-catechine, taxifolin derivatives, procyanidin, and the like separated from *Pinus densiflora*, were secured to be used for evaluation of 5α-reductase inhibitory activity.

Example 3. Confirmation of Activity Inhibitory Effect of 5α-Reductase of *Acanthopanax Sessiliflorus*, *Phragmites* Rhizome, and *Pinus Densiflora* Extracts Testosterone degradation was measured as total testosterone (TT) as the most important indicator shown in menopausal men.

A testosterone measurement method using liquid chromatography is the most standardized method, particularly has high sensitivity when the concentration is low, and is known as the most reliable experiment method capable of being applied to accurate measurement of testosterone.

Specifically, for the total testosterone measurement, 0.02 mM of a phosphate buffer (pH 6.5), 150 μM of testosterone, 50 μM of NADPH and each sample were treated with 200 μl and then reacted for 30 minutes at 37° C. using an enzyme solution obtained from the liver of the rat.

Thereafter, the mixture was added with 500 μl of dichloromethane to terminate the reaction, centrifuged at 3000 rpm for 10 minutes, and then cooled at −50° C. to separate and concentrate an unfrozen organic solvent layer, and thereafter, 1 ml of methanol was added in each sample and diluted to be used as a specimen.

The HPLC analysis conditions of testosterone were shown in the following Tables 1 and 2, and the results were shown in FIG. 1.

The total testosterone content using HPLC was evaluated by considering chemical properties of HPLC analysis conditions of added testosterone, C18 was used as an analytical column, and an area value of testosterone reduced in each obtained sample was calculated, and effects on 5α-reductase of natural polyphenols (acanthoside D, siringin, methyl gallate, P-coumaric acid, lyoniresinol, lyoniresinol-glucopyranoside, catechine, taxifolin, procyanidin B1), an *Acanthopanax sessiliflorus* extract, a *Phragmites* rhizome extract, or a *Pinus densiflora* extract, and a complex extract obtained by mixing the extracts were evaluated.

Finasteride, which has been sold as a 5α-reductase inhibitor on the market, was used as a positive control.

Based on the results, the 5α-reductase inhibitory activity was determined by quantifying by a t-test using an SPSS statistical program.

TABLE 1

HPLC analysis conditions of Complex extract and acanthoside D

| HPLC condition | | | |
|---|---|---|---|
| Column | Kromasil 100-5-$C_{18}$ | | |
| Flow rate | 1 mℓ/min | | |
| UV length | 220 nm | | |
| Injection volume | 10 μℓ | | |
| Mobile solvent | A: 0.2% Acetic acid; B: Acetonitrile | | |
| Mobile Phase | Time (min) | A | B |
| | 0 | 90 | 10 |
| | 40 | 70 | 30 |
| | 42 | 0 | 100 |
| | 52 | 0 | 100 |

TABLE 2

HPLC analysis conditions of Complex extract and P-coumaric acid

| HPLC condition | | | |
|---|---|---|---|
| Column | Kromasil 100-5-$C_{18}$ | | |
| Flow rate | 1 mℓ/min | | |
| UV length | 280 nm | | |
| Injection volume | 10 μℓ | | |
| Mobile solvent | A: 0.2% Acetic acid; B: Acetonitrile | | |
| Mobile Phase | Time (min) | A | B |
| | 0 | 90 | 10 |
| | 40 | 70 | 30 |
| | 42 | 0 | 100 |
| | 52 | 0 | 100 |

As a result, as illustrated in FIG. 2, $IC_{50}$ of finasteride was 11.9, and acanthoside D, of which $IC_{50}$ was 108. 3, had the best 5α-reductase inhibitory activity among the compounds, and in the extracts, the complex extract of *Acanthopanax sessiliflorus*, *Phragmites* rhizome, and *Pinus densiflora* had the highest α-reductase inhibitory activity as $IC_{50}$ 40.9.

Example 4. Confirmation of Efficacy Index Compounds

Based on active compounds separated from *Phragmites* rhizome and *Pinus densiflora* as candidate materials to help in improving benign prostatic hyperplasia, the content and validation of each plant were evaluated and the possibility as a functional material was evaluated.

Specifically, optimal HPLC analysis conditions capable of analyzing the active ingredients in the plant were determined while varying the composition and the flow rate of an organic solvent using HPLC, and then the active ingredient content was determined, and the specificity, accuracy, and precision of the index ingredients were evaluated according to a validation guideline issued by the KFDA.

Conditions used for HPLC analysis are as shown in Tables 1 and 2 above.

4-1. Confirmation of Specificity

Figure 3:
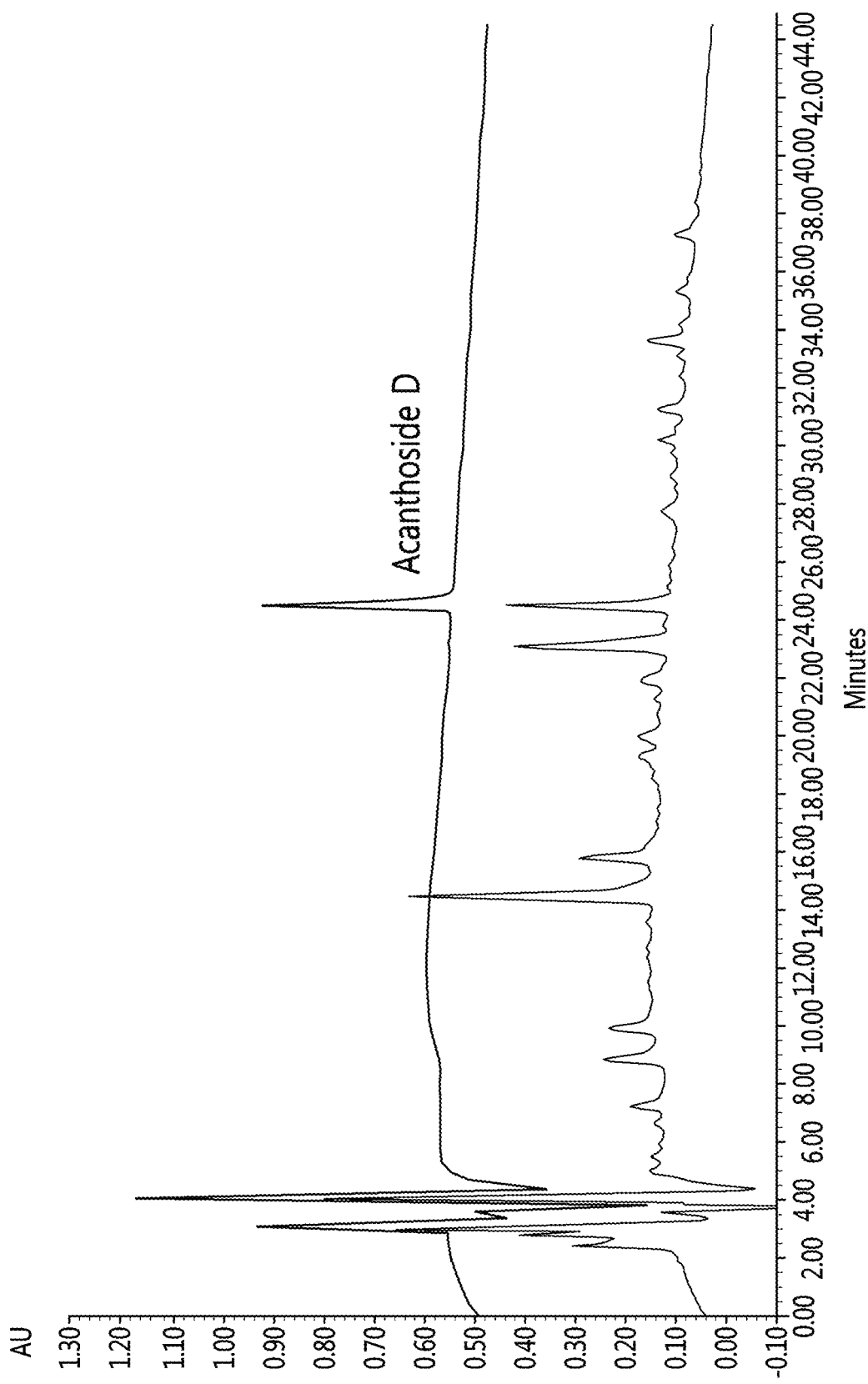
FIG. 3 is a diagram illustrating HPLC results of the complex extract and acanthoside D.
Figure 4:
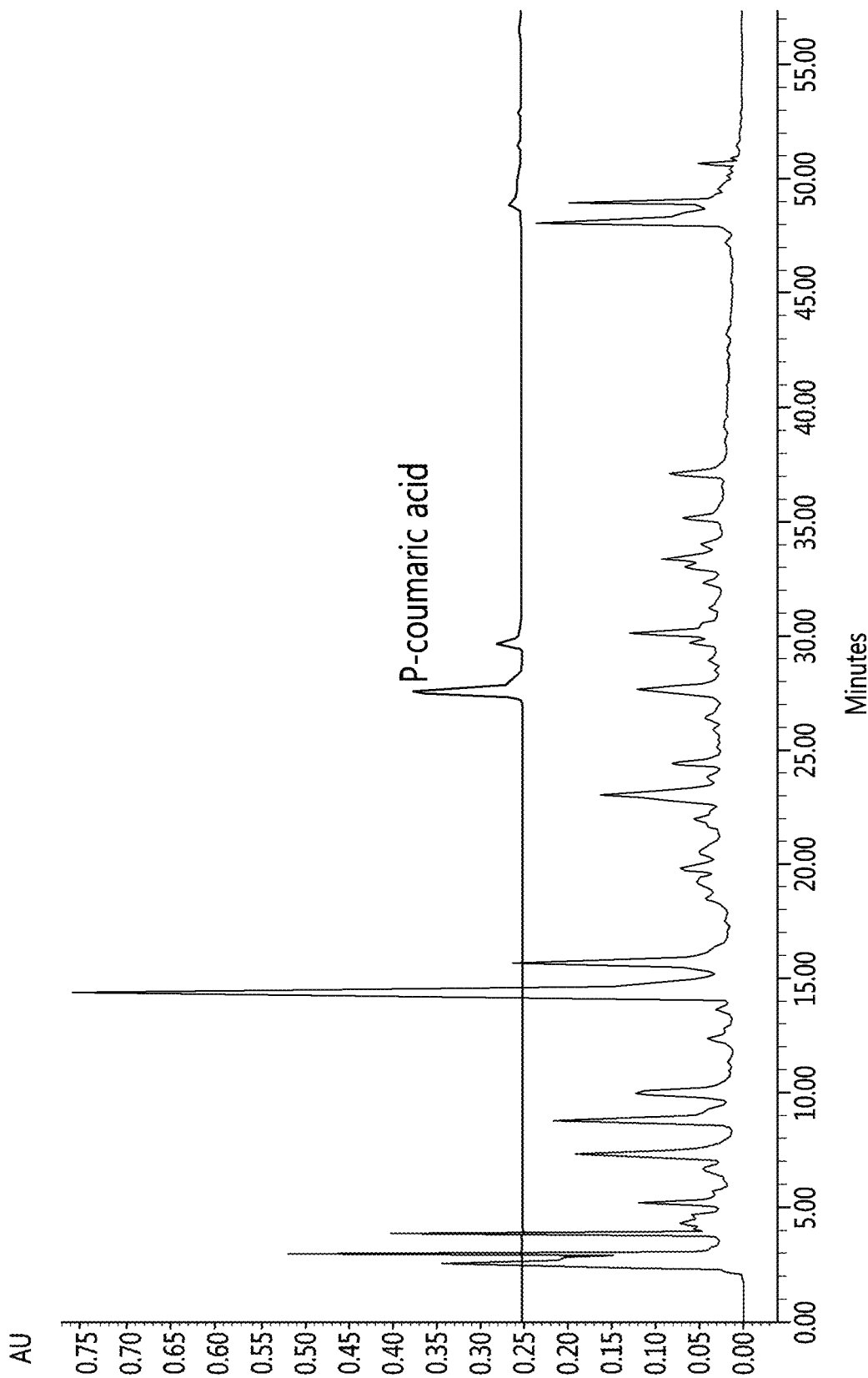
FIG. 4 is a diagram illustrating HPLC results of the complex extract and p-coumaric acid.

Whether peaks of acanthoside D and p-coumaric acid were separated was confirmed by comparing chromatography of the complex extract using HPLC, and as a result, as illustrated in FIGS. 3 and 4, it was confirmed that acanthoside D and p-coumaric acid were separated without interference from other ingredients.

4-2. Confirmation of Calibration Curve and Linearity

Figure 5:
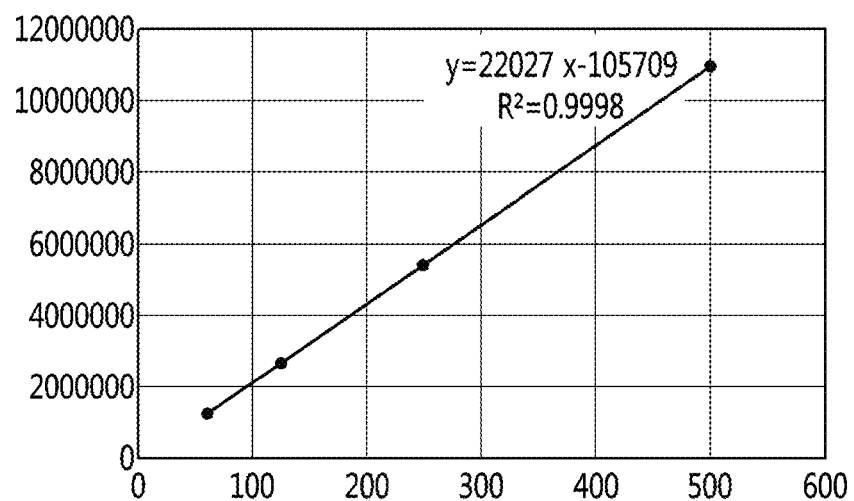
FIG. 5 is a diagram illustrating a calibration curve and linearity of acanthoside D and p-coumaric acid which are efficacy index ingredients of the complex extract.
Figure 5:
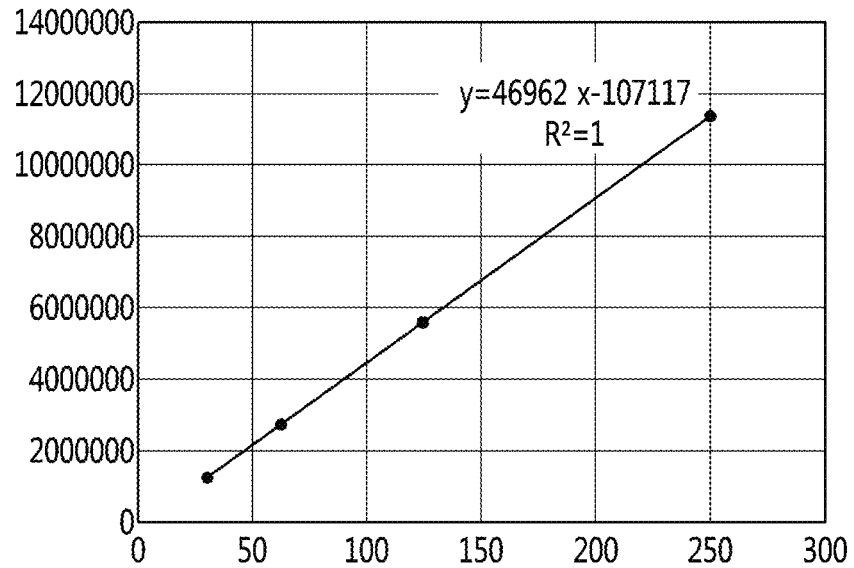

As can be seen in FIG. 5, a linear regression equation of a calibration curve prepared by analyzing acanthoside D using HPLC was Y=22027X−105709 and a correction coefficient ($R^2$) of the calibration curve was 0.9998 to have good linearity, and a linear regression equation of a calibration curve prepared by analyzing p-coumaric acid using HPLC was Y=46962X−107117 and a correction coefficient ($R^2$) of the calibration curve was 1 to have high linearity 4-3. Confirmation of Accuracy and Precision As illustrated in FIG. 6, it was confirmed that accuracy of acanthoside D was confirmed within 96.77 to 101.46% and precision had a good value of 0.46 to 1.13% as a coefficient variation (c.v.).

In addition, it was confirmed that accuracy of p-coumaric acid was confirmed within 96.39 to 100.96% and precision had a good value of 0.12 to 0.62% as a coefficient variation (c.v.).

Example 5. Confirmation of Contents of Acanthoside D and p-Coumaric Acid in Complex Extract of *Acanthopanax Sessiliflorus, Phragmites* Rhizome, and *Pinus Densiflora*

Acanthoside D and p-coumaric acid were set as efficacy indexes, and the contents of the index ingredients of the complex extract prepared in Example 1 were evaluated.

Specifically, the contents of index ingredients were measured using an analysis method established in Tables 1 and 2 above and as a result, it was confirmed that the content of acanthoside D was 1.06% and the content of p-coumaric acid was 0.07% in the complex contract.

Example 6. Western Blotting

5α-reductase had total three types of subtypes (types 1, 2 and 3), in which types 1 and 3 have been studied for diseases such as male hair loss or acne and type 2 was directly associated with benign prostatic hyperplasia.

As a result, in Example 6, a 5α-reductase type 2 (SRD5A2) protein expression level was analyzed by Western blotting to confirm 5α-reductase inhibitory activity.

Specifically, the cells were divided at a concentration of $2.0 \times 10^5$ cell/well and treated with 100 μg/ml of the *Acanthopanax sessiliflorus* extract, 600 μg/ml of the *Pinus densiflora* extract, 600 μg/ml of the *Phragmites* rhizome extract, or 350 μg/ml of the complex extract (Extract 4) obtained by mixing the extracts at 4:2:1 in a PRMI1640 medium containing 1% fetal bovine serum (FBS), and then cultured for 24 hours.

Finasteride, which has been sold as a 5α-reductase inhibitor on the market, was used as a positive control.

Information on each extract and each compound treated on the cells was shown in Table 3 below.

Figure 7:
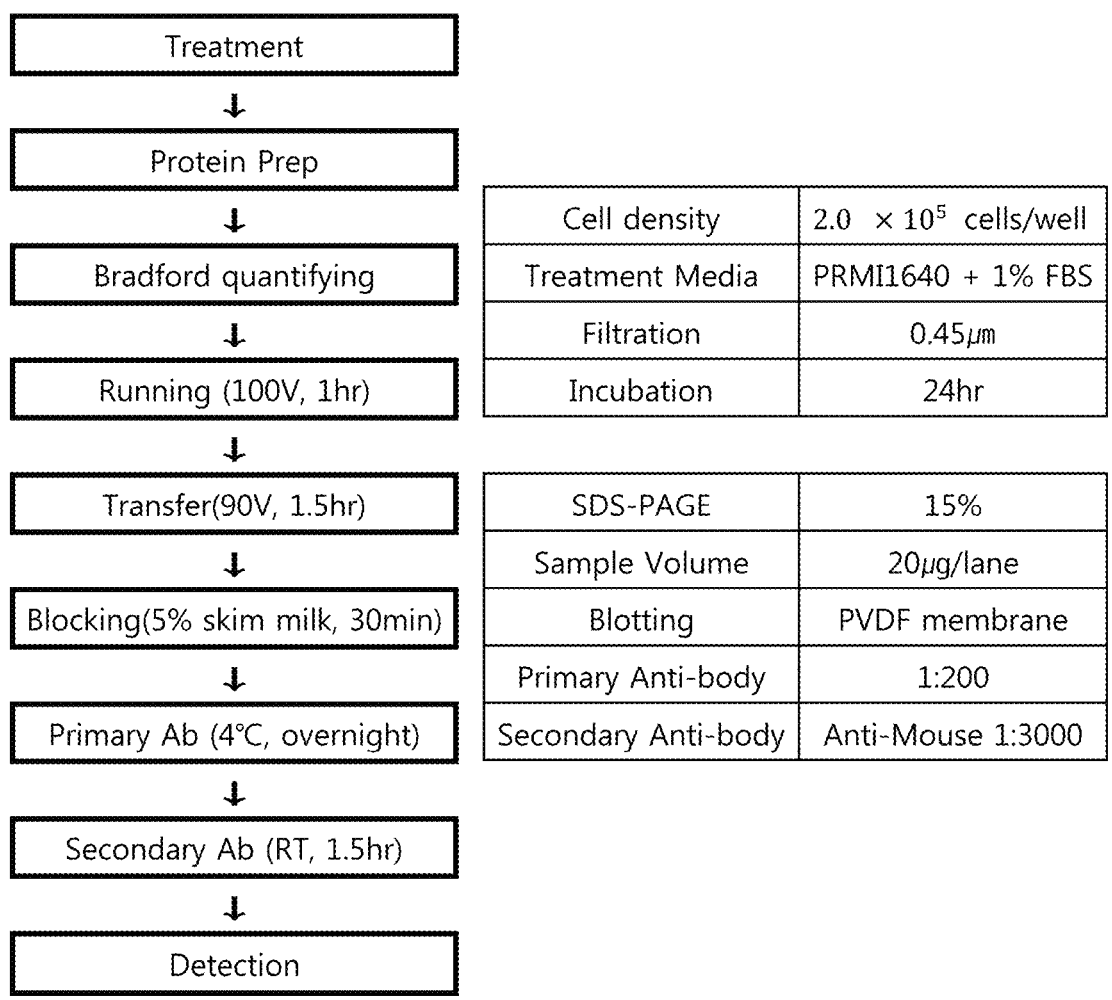
FIG. 7 is a diagram illustrating a procedure and conditions for Western blotting of the complex extract.

Then, the cultured cells were lysed, filtered with a 0.45 μm mesh, and subjected to Western blotting according to a procedure shown in FIG. 7.

Specifically, a primary antibody (Anti-SRD5A2, Sigma) was diluted to 1:200 and treated, and a secondary antibody (m-IgGP-HRP, Santa Cruz) was diluted to 1:3000 and treated, and then the expression levels of 5α-reductase type 2 according to treatment of each extract and each compound were confirmed.

The information on the used antibody was shown in Table 4 below.

TABLE 3

| Classification | | concentration |
| --- | --- | --- |
| Extract 1 | pinus densiflora | 600 μg/ml |
| Extract 2 | phragmites rhizome | 600 μg/ml |
| Extract 3 | acanthopanax sessiliflorus | 100 μg/ml |
| Extract 4 | mixed (complex extract) | 350 μg/ml |
| Compound 1 | P-Coumaric Acid | 0.40 mM |
| Compound 2 | Acanthoside D | 0.40 mM |
| Compound 3 | (+)-Catechin | 0.40 mM |
| Compound 4 | Fiasteride | 40 μg/ml |

TABLE 4

| Classification | | manufacturer | Cat. # |
| --- | --- | --- | --- |
| Primary Ab | Anti-SRD5A2 | Sigma | WH0006716M1 |
| | B-actin | Santa Cruz | SC-69879 |
| Secondary Ab | m-IgGk BP-HRP (Anti-Mouse) | Santa Cruz | SC-516102 |

Figure 8:
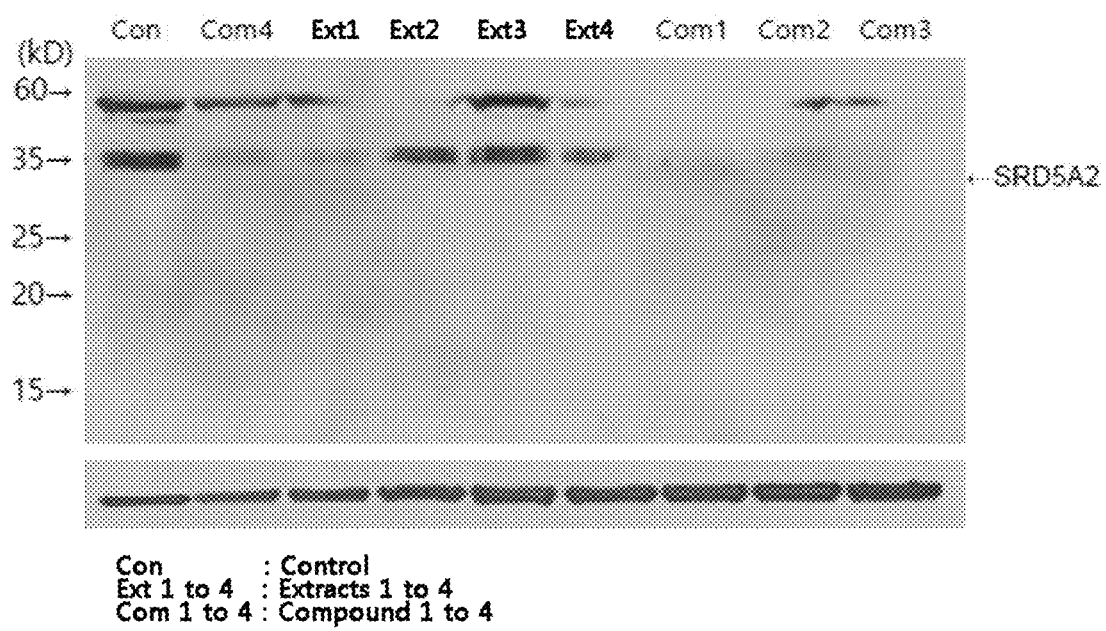
FIG. 8 is a diagram for confirming a decrease in the expression level of a 5α-reductase type 2 protein according to the treatment of the complex extract, through Western blotting.

As a result, as shown in FIG. 8, the expression levels of the 5α-reductase type 2 according to treatment of each extract, the complex extract, and each compound were confirmed, and particularly, in the case of treating the complex extract (Extract 4) obtained by mixing *Acanthopanax sessiliflorus, Phragmites* rhizome, and *Pinus densiflora* at 4:2:1, it was confirmed that the expression level of the 5α-reductase type 2 was significantly reduced as compared with the case of treating finasteride as the 5α-reductase inhibitor sold on the market.

Further, even in the case of treating acanthoside D (compound 2) and p-coumaric acid (compound 1) as index ingredients of the complex extract, it was confirmed that the expression levels of 5α-reductase type 2 were significantly reduced, it can be seen that acanthoside D and p-coumaric acid had high activity on 5α-reductase inhibition, and it was confirmed that the complex extract obtained by mixing *Acanthopanax sessiliflorus, Phragmites* rhizome, and *Pinus densiflora* at a proper ratio of 4:2:1 had excellent 5α-reductase inhibitory activity.

The content of acanthoside D and the content of p-coumaric acid in the combined extracts were 1.06% and 0.07%, respectively, and it is suggested that the complex extract may be used as a natural functional material for improving and preventing the prostate disease.

The aforementioned description of the present invention is to be exemplified, and it can be understood by those skilled in the art that the technical spirit or required features of the present invention can be easily modified in other detailed forms without changing. Therefore, it should be appreciated that the aforementioned exemplary embodiments described above are all illustrative in all aspects and are not restricted.

The invention claimed is:

1. A pharmaceutical composition for treating a prostate disease containing therapeutically effective amounts of extracts of *Acanthopanax sessiliflorus, Phragmites* spp. rhizome and *Pinus densiflora*, as active ingredients, wherein the prostate disease is prostate cancer or benign prostatic hyperplasia, and wherein the composition includes 2 to 5 parts by weight of the *Acanthopanax sessiliflorus* extract and 1 to 3 parts by weight of the *Phragmites* rhizome extract with respect to 1 part by weight of the *Pinus densiflora* extract.

2. The pharmaceutical composition for treating prostate diseases of claim 1, wherein the composition inhibits 5α-reductase activity.

3. The pharmaceutical composition for treating prostate diseases of claim 1, wherein the *Acanthopanax sessiliflorus, Phragmites* spp. rhizome and *Pinus densiflora* extracts are made by extraction with at least one solvent selected from the group consisting of water, alcohols having 1 to 4 carbon atoms, n-hexane, ethyl acetate, acetone, butyl acetate, 1,3-butylene glycol, methylene chloride, and solvent mixtures thereof.

4. The pharmaceutical composition for treating prostate diseases of claim 1, wherein the composition includes 4 parts by weight of the *Acanthopanax sessiliflorus* extract and 2 parts by weight of the *Phragmites* rhizome extract with respect to 1 part by weight of the *Pinus densiflora* extract.

5. A health functional food composition for improving a prostate disease containing therapeutically effective amounts of extracts of *Acanthopanax sessiliflorus, Phragmites* spp. rhizome and *Pinus densiflora* as active ingredients, wherein the prostate disease is prostate cancer or benign prostatic hyperplasia, and wherein the composition includes 2 to 5 parts by weight of the *Acanthopanax sessiliflorus* extract and 1 to 3 parts by weight of the *Phragmites* rhizome extract with respect to 1 part by weight of the *Pinus densiflora* extract.

6. The health functional food composition for improving prostate diseases of claim 5, wherein the composition inhibits 5α-reductase activity.

7. The health functional food composition for improving prostate diseases of claim 5, wherein the *Acanthopanax sessiliflorus, Phragmites* spp. rhizome and *Pinus densiflora* extracts are made by extraction with at least one solvent selected from the group consisting of water, alcohols having 1 to 4 carbon atoms, n-hexane, ethyl acetate, acetone, butyl acetate, 1,3-butylene glycol, methylene chloride, and solvent mixtures thereof.

\* \* \* \* \*